United States Patent [19]
Welch

[11] Patent Number: 5,309,927
[45] Date of Patent: May 10, 1994

[54] CIRCULAR STAPLER TISSUE RETENTION SPRING METHOD

[75] Inventor: Robert F. Welch, Downingtown, Pa.

[73] Assignee: Ethicon, Inc., Somerville, N.J.

[21] Appl. No.: 964,734

[22] Filed: Oct. 22, 1992

[51] Int. Cl.$^5$ .................................... A61B 17/115
[52] U.S. Cl. .................................... 128/898; 227/179
[58] Field of Search ............... 606/153, 154; 227/175, 227/179, 180, 181, 902, 176, 177, 178; 267/166, 166.1; 128/898

[56] References Cited

U.S. PATENT DOCUMENTS

| | | | |
|---|---|---|---|
| 4,017,062 | 4/1977 | Zwirner | 267/166 |
| 4,120,489 | 10/1978 | Borlinghaus | 267/166.1 |
| 4,476,863 | 10/1984 | Kanshin et al. | 606/153 |
| 4,592,354 | 6/1986 | Rothfuss | 227/179 |
| 4,665,917 | 5/1987 | Clanton et al. | 606/153 |
| 5,104,025 | 4/1992 | Main et al. | 227/179 |

FOREIGN PATENT DOCUMENTS

1509052  9/1989  U.S.S.R. .................... 227/175

Primary Examiner—Tamara L. Graysay
Attorney, Agent, or Firm—E. R. Skula

[57] ABSTRACT

An tissue retention spring for use with a surgical circular stapler used to perform an anastomosis. The tissue retention spring is mounted onto the anvil shaft of the stapler. The spring has a plurality of connected helical coils defining a member having an axial passage therethrough. The spring provides tissue retention, tissue and fluid venting, and improved stapler closing.

13 Claims, 6 Drawing Sheets

CIRCULAR STAPLER TISSUE RETENTION SPRING METHOD

TECHNICAL FIELD

The field or art to which this invention pertains is surgical instruments, in particular, circular surgical staplers.

BACKGROUND OF THE INVENTION

Surgical staplers have been long known in the surgical arts as a quick and efficient way of joining or repairing tissue. Stapling has become an accepted alternative to suturing. In certain types of surgical procedures the use of surgical staples has become the preferred method of joining tissue, and, specially configured surgical staplers have been developed for these applications. For example, intra-luminal or circular staplers have been developed for use in a surgical procedure known as an anastomosis.

Circular staplers are well known in this art. Circular staplers useful to perform an anastomosis are disclosed in U.S. Pat. No. 5,104,025 which is incorporated by reference. A conventional circular stapler typically consists of an elongated shaft having a proximal actuating mechanism and a distal stapling mechanism mounted to the shaft. The distal stapling mechanism typically consists of a fixed stapling cartridge containing a plurality of staples configured in a concentric circular array. A round cutting knife is concentrically mounted in the cartridge interior to the staples. The knife is moveable in an axial, distal direction. Extending axially from the center of the cartridge is a trocar shaft. The trocar shaft is moveable, axially, with respect to the cartridge and elongated shaft. An anvil member is mounted to the trocar shaft. The anvil member has a conventional staple anvil mounted to it for forming the ends of staples. The distance between the distal face of the staple cartridge and the staple anvil can be controlled by an adjustment mechanism mounted to the proximal end of the stapler shaft. Tissue contained between the staple cartridge and the staple anvil is simultaneously stapled and cut when the actuating mechanism is engaged by the surgeon.

An anastomosis is a surgical procedure wherein sections of intestine are joined together after a connecting section has been excised. The procedure requires joining the ends of two tubular sections together to form a continuous tubular pathway. Previously, this surgical procedure was a laborious and time consuming operation. The surgeon had to precisely cut and align the ends of the intestine and maintain the alignment while joining the ends with numerous suture stitches. The development of circular staplers has greatly simplified the anastomosis procedure and also decreased the time required to perform an anastomosis.

When performing an anastomosis using a circular stapler, typically, the intestine is stapled using a conventional surgical stapler with double rows of staples being emplaced on either side of a target section (i.e., specimen) of intestine. The target section is typically simultaneously cut as the section is stapled. Next, after removing the specimen, the surgeon typically inserts the anvil head (anvil member) into the proximal end of the lumen, proximal of the staple line. This is done by inserting the anvil head into an entry port cut into the proximal lumen by the surgeon. On occasion the anvil head can be placed transanally, by placing the anvil head on the distal end of the stapler and inserting the instrument through the rectum. Typically the distal end of the stapler is inserted transanally. The surgeon then typically ties the proximal end of the intestine to the anvil shaft using a suture or other conventional tying device. Next, the surgeon cuts excess tissue adjacent to the tie and the surgeon attaches the anvil to the trocar shaft of the stapler. The surgeon then closes the gap between the anvil and cartridge, thereby engaging the proximal and distal ends of the intestine in the gap. The surgeon next actuates the stapler causing several rows of staples to be driven through both ends of the intestine and formed, thereby joining the ends and forming a tubular pathway. Simultaneously, as the staples are driven and formed, a concentric circular blade is driven through the intestinal tissue ends, cutting the ends adjacent to the inner row of staples. The surgeon then withdraws the stapler from the intestine and the anastomosis is complete.

In order to assist the surgeon in performing an anastomosis, various accessories have been developed for use with a circular stapler. One such type of accessory is known as an anvil bushing and is disclosed in U.S. Pat. No. 4,592,354. The anvil bushing disclosed in that patent consists of two flanges separated by a shank member. The shank member has a cylindrical pathway running therethrough. The diameter of the cylindrical pathway is sized so that the spool is in frictional engagement with the anvil shaft. The spool is used as a tissue attachment or retention means wherein intestine is sutured or tied about the spool, and, the intestine may be cut adjacent to the spool.

U.S. Pat. No. 4,665,917 discloses an improved intraluminal stapler having a clamping means disposed on the anvil shaft. The clamping means consists of a circular array of barbs extending outwardly to grasp the ends of the intestine.

Although conventional anvil bushings have many advantages and have proven to be beneficial when used with a circular stapler, it is also known that there are disadvantages associated with their use. The anvil bushings must be mounted by the surgeon or an assistant on the anvil shaft prior to use. It is often difficult to precisely position the bushings on the anvil shaft in an optimal position to facilitate tying. It is also known that the presence of the anvil bushing may increase the closing force necessary to position the anvil in proximity to the cartridge to effectively allow stapling and cutting. It is additionally known that it is sometimes difficult to locate the proximal edge of the anvil bushing when the surgeon attempts to cut the intestine. Furthermore, it is also known that the mucosa of the intestine is extremely slippery and that it is difficult to retain the intestine on a conventional anvil bushing.

Therefore, what is needed in this art are new devices for use with a circular stapler which facilitate the use of a circular stapler in an anastomotic procedure and eliminate the disadvantages of existing anvil bushings.

Accordingly, it is an object of the present invention to provide a tissue retention spring for an anastomotic procedure which can be precisely located on an anvil shaft during a surgical anastomotic procedure.

It is yet another object of the present invention to provide a tissue retention spring which decreases the force required to close an anvil by providing tissue and fluid venting.

It is yet a further object of the present invention to provide a tissue retention spring which facilitates tissue cutting.

It is still a further object of the present invention to provide a tissue retention spring which has enhanced tissue grasping and retention and which provides additional length to which tissue may be tied.

SUMMARY OF THE INVENTION

A tissue retention spring for a surgical, circular stapler is disclosed. The spring comprises a helical coil spring member having a proximal end, a distal end and a plurality of adjacent, connected coils defining a spring member. The coils are separated by axial spaces. The spring has an axial passage therethrough. The tissue retention spring is placed upon the shaft of an anvil member of a circular stapler.

Another aspect of the present invention is the combination of a circular stapler and the above-described tissue retention spring.

Yet another aspect of the present invention is a method of using the above-described tissue retention spring in an endoscopic surgical procedure.

Still yet another aspect of the present invention is a method of retaining tissue on a circular stapler. The method comprises initially concentrically placing the above-described tissue retention spring onto the anvil shaft of a circular stapler. Then, tissue is placed about the spring. Finally, the spring is compressed thereby engaging at least some of the tissue between the coils of the spring. Preferably, the tissue is tied to the spring with at least one suture prior to compressing the spring.

DESCRIPTION OF THE PREFERRED EMBODIMENTS

The disclosures of U.S. Pat. Nos. 4,592,254 and 4,665,917 are incorporated by reference.

Figure 1:
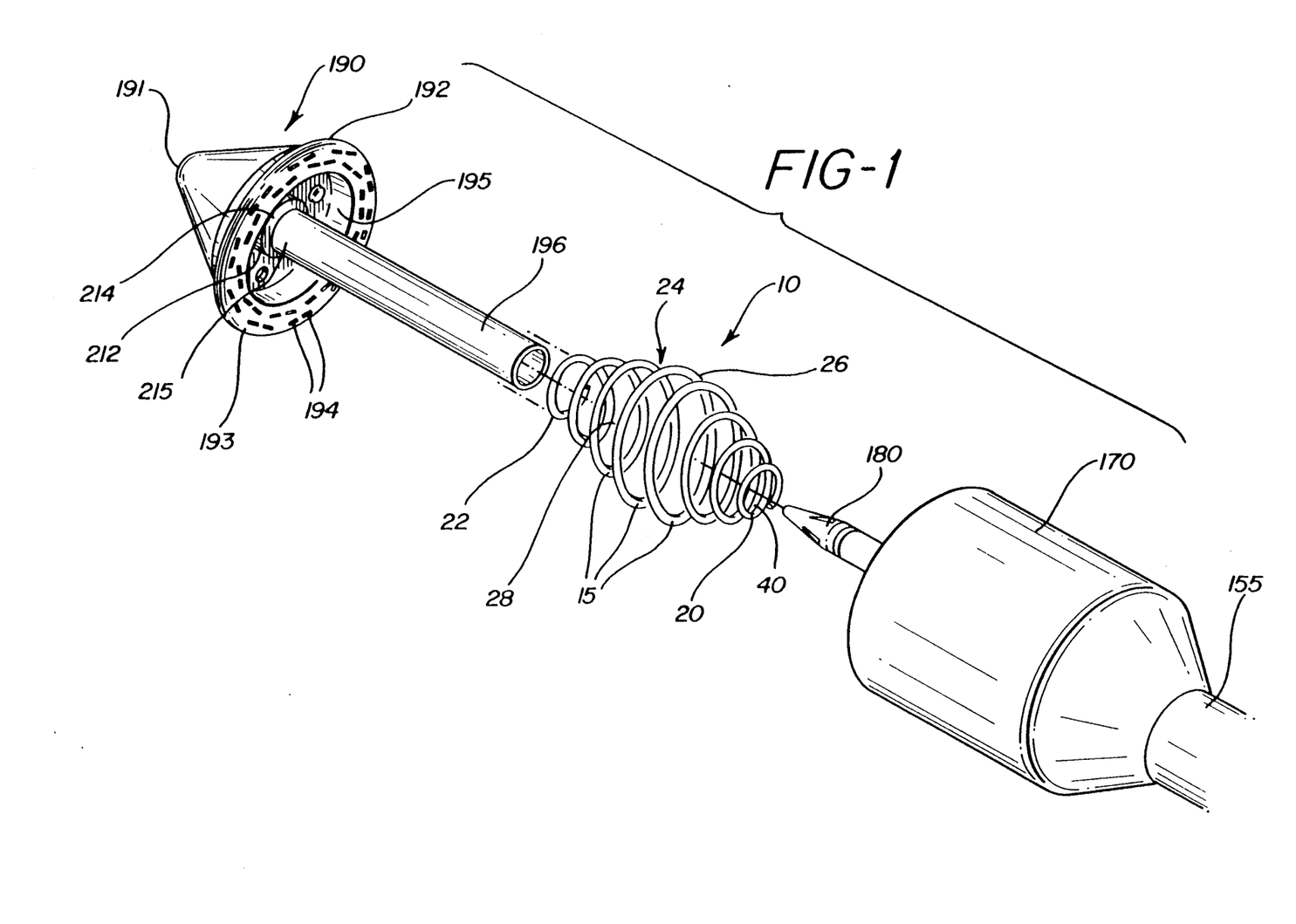
FIG. 1 is a perspective view of the tissue retention spring the present invention.
Figures 2, 2A:
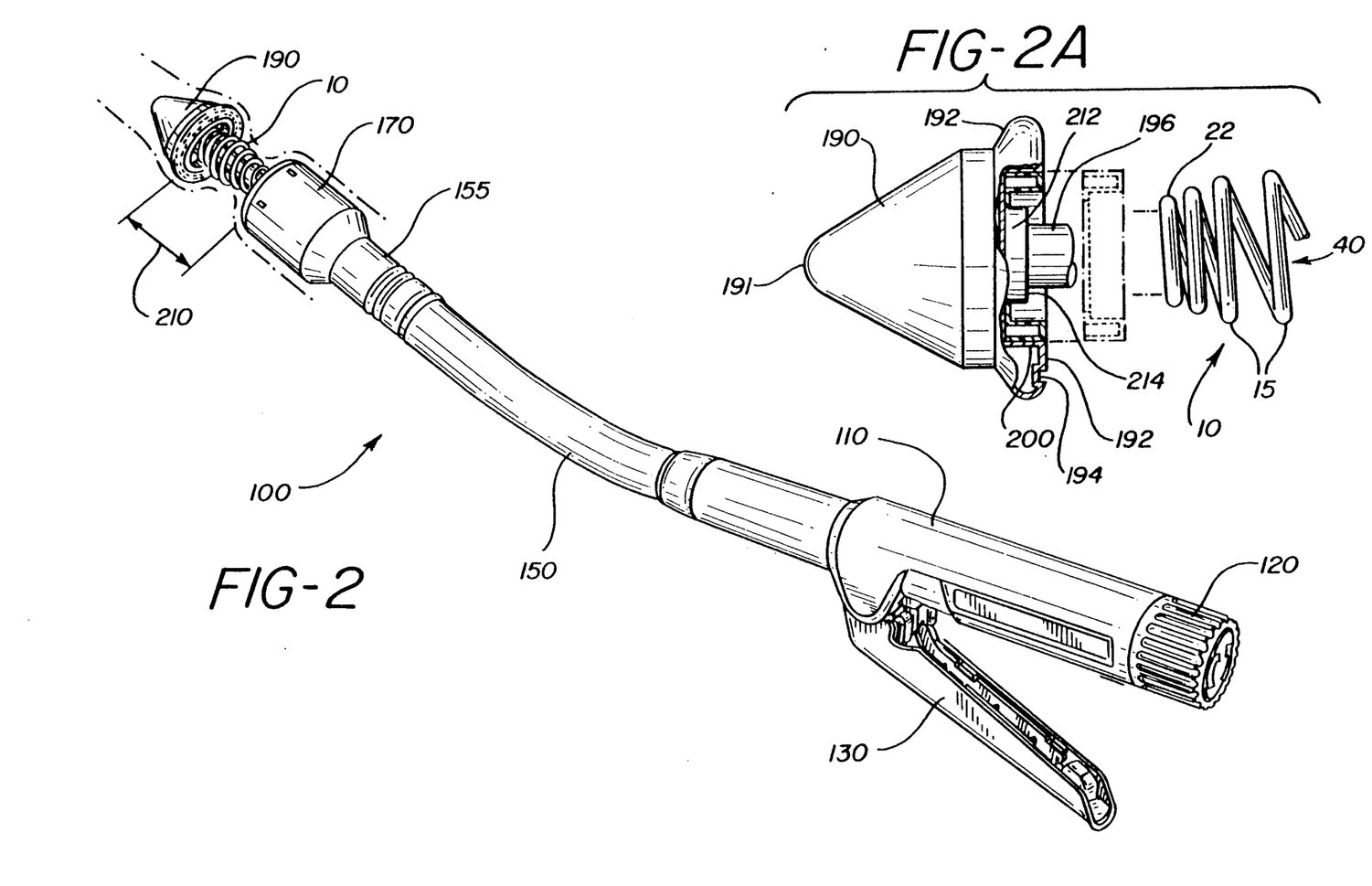
FIG. 2 is a perspective view of the tissue retention spring of the present invention mounted to a conventional circular stapler.
FIG. 2A is an enlarged partial cross-sectional view of the anvil member of the circular stapler of FIG. 2.
Figure 4:
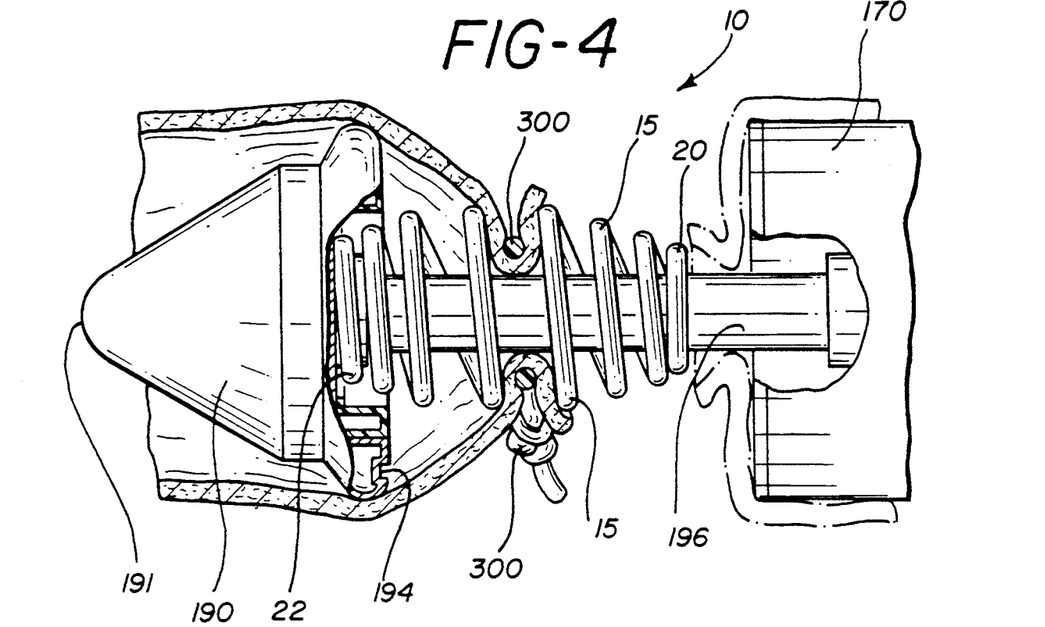
FIG. 4 illustrates the tissue retention spring of the present invention mounted on a circular stapler anvil shaft in a sectional view of an intestine during an anastomosis prior to closing the anvil gap.
Figure 5:
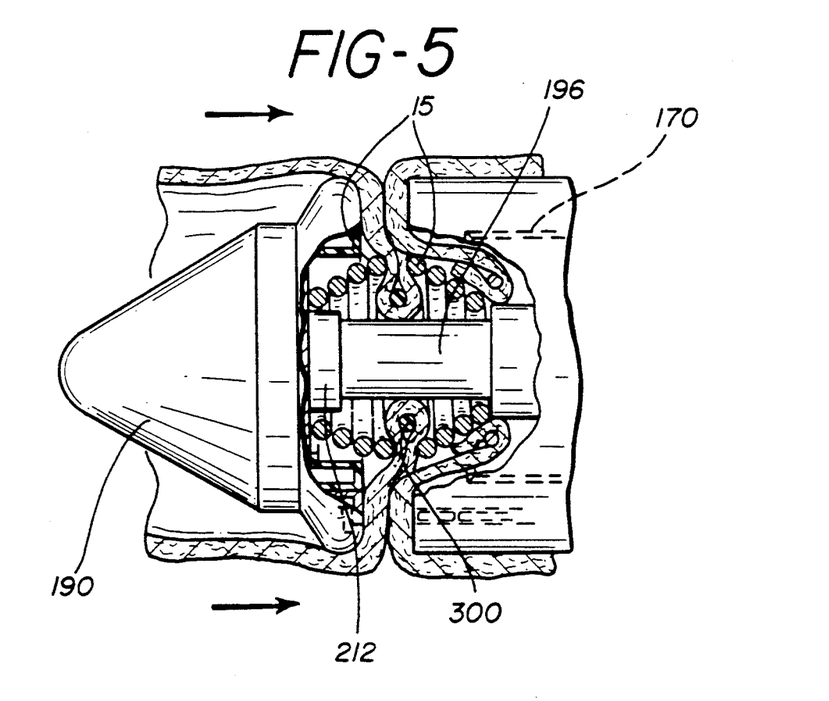
FIG. 5 illustrates the tissue retention spring of FIG. 4 after the anvil gap has been closed and immediately prior to actuation of the staples and cutting blade.
Figure 6:
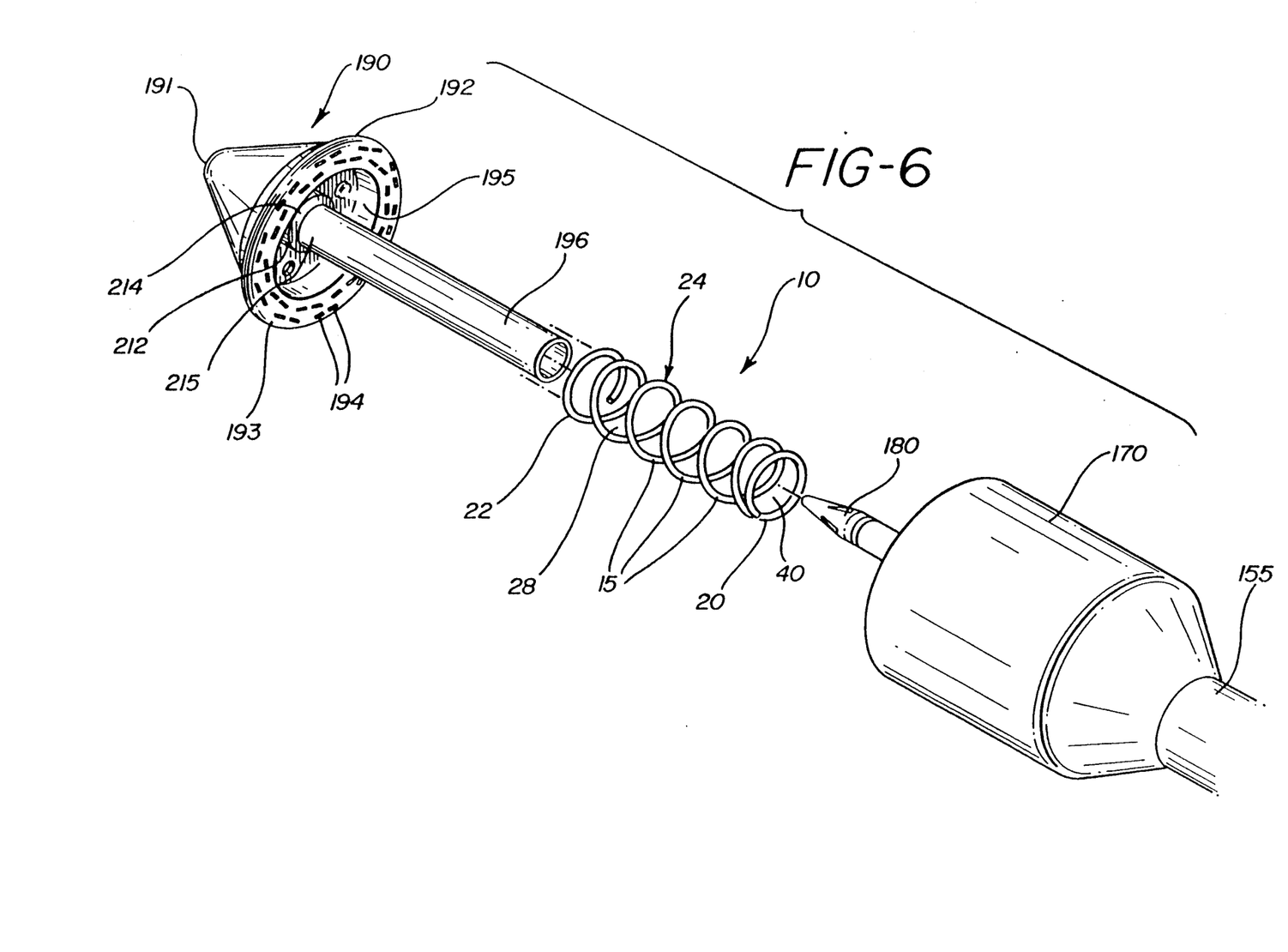
FIG. 6 is a perspective view of the tissue retention spring of the present invention schematically showing wherein the coils have a constant diameter and the spacing between the coils is constant.
Figure 7:
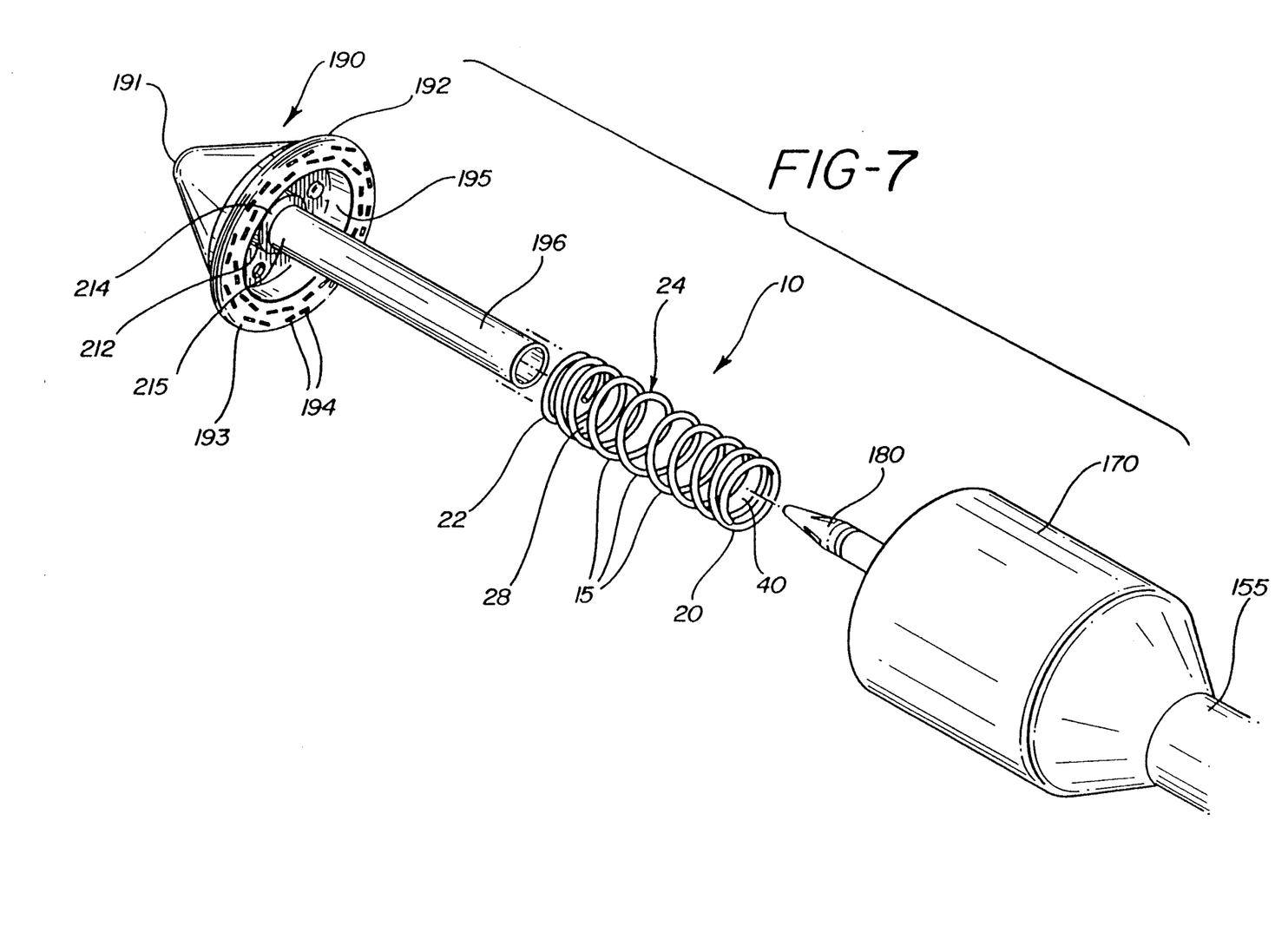
FIG. 7 is a perspective view of the tissue retention spring of the present invention schematically showing wherein the coils have a constant diameter and the spacing between the coils varies.

The tissue retention spring 10 of the present invention is seen in FIGS. 1-7. Referring to FIGS. 1, 2 and 2A, the tissue retention spring 10 is seen to consist of a plurality of connected coils 15. The spring 10 is seen to have an inner axial passageway 40 for receiving a shaft. The spring 10 is seen to have a proximal end 20 and a distal end 22 and an elongated section 24 between proximal end 20 and distal end 22. The spring 10 may have a constant diameter along its length, as schematically illustrated in FIGS. 6 and 7, or a variable diameter as illustrated in FIG. and FIG. 4. For example, the diameter of proximal end 20 and distal end 22 may be of equal size while the diameter of the section 24 increases to a maximum at the center 26 of the spring member 10. That is, starting at either end, each succeeding coil 15 would be of an increasing diameter up to a maximum diameter at the center 26 of the spring 10. The distance 28 between the coils 15 will be sufficient to provide effective tissue retention. Similarly, the distance 28 may be constant or may vary between adjacent coils 15 when the spring 10 is in the uncompressed state, as schematically illustrated in FIGS. 6 and 7. The spaces 28 will typically decrease in size as spring 10 is compressed.

The inner mucosal layer of an intestine is known to consist of a slippery mucous membrane and the tissue retention spring 10 assists in retaining the intestinal tissue about the anvil member shaft 196. As the stapler gap 210 is closed, mucosal tissue will be positively retained in at least one of the spaces 28 by compression of the coils 15. Another function of the spring 10 is to facilitate closure of the stapler 100. Referring to FIGS. 4 and 5, as the stapler 100 is closed, the intestinal tissue is compressed in the gap 210 between the distal end of the staple cartridge 170 and the anvil 193 of the anvil member 190. The spaces 28 between the coils 15 provide a pathway for tissue, liquids and gases to flow into, thereby providing a venting which facilitates closure of the gap 210 between the distal end of the cartridge 170 and the anvil 193. As previously mentioned, the coils 15 and the spaces 28 also assist in retaining the mucosa of the intestine by capturing the mucosa in the spaces 28 when spring 10 is compressed.

Referring to FIG. 2, the tissue retention spring 10 of the present invention is seen mounted to a conventional circular stapler 100. The circular stapler 100 has proximal handle 110 mounted to an elongated tubular frame 150. Mounted to the distal end 155 of the elongate tubular frame 150 is the cartridge head 170. The cartridge head 170 contains a plurality of conventional staples (not shown) arranged in a circular array to provide concentric rows of formed staples. The cartridge 170 also contains a cylindrical, circular knife (not shown) having a cutting edge for cutting tissue interior to the rows of formed staples. The handle 110 is seen to have mounted to its proximal end the knob 120 which can be rotated to increase or decrease the gap 210 between the cartridge head 170 and the anvil member 190. Also mounted to the handle 110 is the actuating lever 130 for actuating the driving of the staples and the engagement of the knife. Extending from the cartridge 170 is the trocar shaft 180. The trocar shaft 180 is moveable, axially, distally and proximally by rotating the knob 120 either clockwise or counterclockwise.

As can be seen in FIGS. 1-5, the anvil member 190 is seen to be a cylindrical member having a tapered distal end 191 and a flat proximal end 192 for mounting circular, conventional anvil 193. Anvil 193 is seen to have forming cavities 194 for forming the ends of staples. Mounted to the proximal end 192 of anvil member 190 is the anvil member shaft 196 which extends axially from cavity 195 contained in the proximal end 192 of anvil member 190. The anvil shaft 196 is a cylindrical, tubular member which is mounted on the trocar shaft 180. Concentrically mounted in the cavity 195 on the interior side of the anvil 193 is the breakaway washer 200. The breakaway washer 200 is sized to engage the cutting edge of circular knife when the knife is actuated. Preferably, the washer 200 is designed to split( i.e., the yield point is exceeded) when engaged by the knife such that an inner annular section is disengaged from the washer 200 while an outer annular portion of the washer remains engaged in the cavity 195. Also concentrically mounted in the cavity 195 is the shoulder 212. The shoulder 212 is seen to be a tubular member having internal passage 215 and proximal face 214. The anvil shaft 196 is concentrically mounted to anvil member 190 through passage 215 in the shoulder 212.

The tissue retention spring 10 is mounted or placed onto the shaft 196 by sliding the distal end 22 of the spring 10 onto the shaft 196 and positioning the spring 10 such that the distal end 22 is in contact with the proximal face 214 of the shoulder 212, thereby properly locating the anvil bushing on the anvil shaft 196. The distal end 22 may also be located about the shoulder 212. When the anvil member 190 is mounted onto the trocar shaft 180 by concentrically mounting the anvil shaft 196 onto the trocar shaft 180, the circular stapler is ready for use. Referring to FIG. 2 and FIG. 4, as the gap 2!0 is closed by actuating the knob 120, the proximal end 210 of the spring 10 will come into contact with the distal face of the cartridge 170 thereby causing the spring 10 to compress as it slides distally with respect to the anvil member 190 on the anvil shaft 196. As the spring 10 slides, the coils 15 displace longitudinally with respect to each other causing the width of spaces 28 between the coils 15 to decrease and compressing tissue between coils 15. The distal end 22 slides over and about the shoulder 212 (if not previously placed about shoulder 212), however the distal end 22 may also be designed to have an opening smaller than the diameter of shoulder 212 so that it cannot slide about shoulder 212. The gap 210 can be decreased until the spring 10 is substantially fully compressed. The length of a fully compressed spring 10 without tissue engaged between the coils will be equal to the sum of the thickness of each coil. However if tissue is present, this length will be increased depending upon the type of tissue and the amount of tissue engaged in the spaces 28 between the coils 15.

The interior passage 40 of the spring 10 will be sufficiently sized to provide an effective fit on anvil shaft 196. The dimensions of the interior passage 40 will vary with the size of the anvil shaft 196 and will typically vary along the axial length of the spring 10, but may also be constant. For example, the maximum diameter of passage 40 may be about 0.350 inches to about 0.360 inches, more typically about 0.355 inches, and preferably about 0.355 inches. Similarly, the other dimensions of spring 10 will vary with the size of the particular circular stapler employed and will similarly be sufficient to allow the spring 10 to function effectively. For example, for a particular circular stapler, the length of the spring 10 may be about 0.875 inches to about 1.000 inches, more typically about 0.880 inches to about 0.900 inches, and preferably about 0.885 inches. For example, the diameter of the proximal end 20 and distal end 22 may typically range from about 0.385 inches to about 0.400 inches, more typically about 0.390 inches to about 0.400 inches, and preferably about 0.397 inches.

The spring 10 is made in a conventional manner as will be later discussed herein, e.g., from a wire or other cylindrical member by winding about a mandrel, etc. The wire will typically have a diameter effective to provide the desired spring characteristics. The spaces 28 between the coils 15 will be of sufficient axial length to provide effective tissue retention and venting. Typically the size of space 28 will be determined by factors including the size of the instrument and the number of coils 15 in the spring 10. The spaces 28 may be constant or may vary between coils 15. The spring constant for the spring 10 of the present invention will be sufficient to allow effective closing of the of the stapler 100.

The spring 10 of the present invention may be used with a circular stapler 100 to perform an anastomosis in the following manner, as seen in FIG. 4 and FIG. 5. After a patient has been prepared and anesthetized in accordance with conventional surgical techniques, the surgeon, using conventional surgical techniques, inserts the anvil member 190 and the cartridge 170 of a circular stapler 100 into a section of intestine proximate to a section of intestine targeted for removal. The gap 210 is typically opened to a maximum. Prior to inserting the anvil member 190 and cartridge 170 into the section of intestine, the surgeon places the tissue retention spring 10 onto the anvil shaft 196 by sliding the distal end 22 of the spring 10 onto the anvil shaft 196 and positioning the spring 10 on the anvil shaft 196 by locating the spring 10 such that the distal end 22 engages the shoulder 212. The surgeon then ties a section of the intestine to the spring 10 using a conventional suture (or equivalent thereof) such that the sutured intestine contacts the coils 15 and at least some tissue is forced into at least one space 28. The surgeon then locates the next coil 15 proximal of the secured intestine captured in loop 300 and then cuts the intestine using the next coil 15 of the spring 10 as a cutting guide. The proximal end 20 of spring 10 may have a larger diameter than the distal end 22. The presence of the larger diameter proximal end 20 enables the surgeon to readily identify the proximal end 20 of the spring 10. Next, the target section of intestine is surgically removed and the end of the intestine proximate to the target section that has been removed is tied to the anvil shaft 196 or the spring 10 using conventional suturing methods such as a purse string tie. The gap 210 is then closed, compressing the spring 10 and thereby engaging tissue in the gap 210 and between the coils 15 in at least one space 28. Then, the two sections of intestine are stapled and the intestine ends are simultaneously cut by actuating the lever 130 of the stapler 100 causing staples to be driven from the cartridge head 170 into the cavities 194 of anvil 193 thereby forming the staples. Simultaneously, the knife is driven forward cutting an interior section of intestine adjacent to the anvil 193. The anvil member 190, the cartridge head 170, the stapler 100 and the cut pieces of intestine ends and sutures along with the tissue retention spring 10 are removed from the patient. The anastomosis is then complete and any access openings are sutured or stapled in accordance with conventional surgical procedures. Those skilled in the art will appreciate that, although it is preferred to tie intestine to the spring 10 with a suture, the suture tie may be eliminated if one were willing to accept the disadvantages which may be present, if any.

Figure 3:
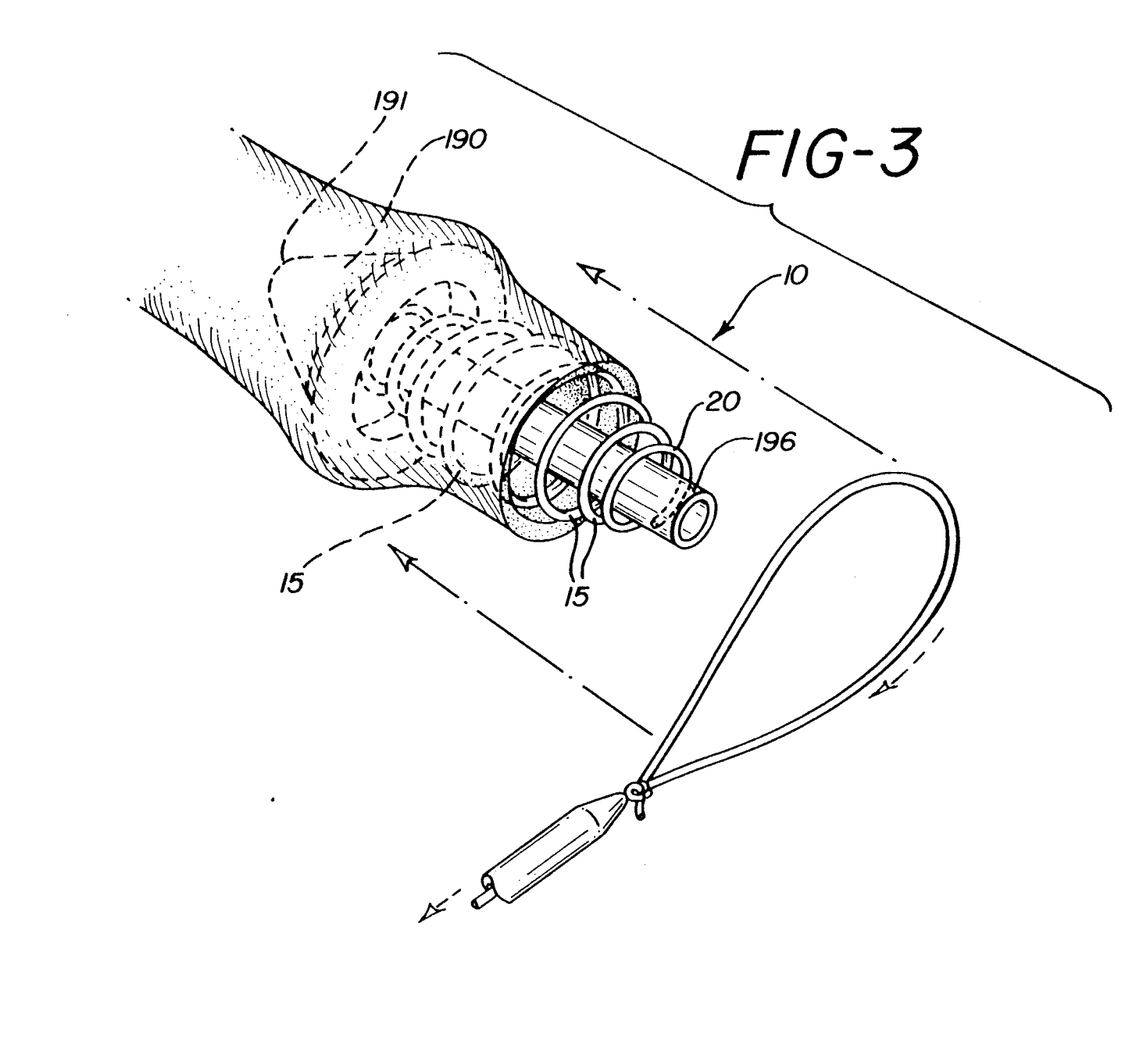
FIG. 3 illustrates a tissue retention spring of the present invention on an anvil shaft in a section of intestine prior to tying the intestine to the spring with a suture during an anastomosis.

A preferred method of using the tissue retention spring 10 of the present invention is with a double staple technique wherein a target section of lumen, or specimen, is cut out from the intestine after stapling on both sides of the section with double rows of staples. The anvil member 190, having the tissue retention spring 10 properly mounted thereto, is then inserted into the proximal lumen adjacent to the proximal staple line after making an incision in the bowel lumen. Referring to FIG. 3 and FIG. 4, the lumen is then secured to the spring 10 using a suture, preferably a preformed loop suture 300 such as an ENDOLOOP ® suture manufactured by ETHICON, Inc., Somerville, N.J. Redundant tissue is then trimmed using the next, coil 15 as a cutting guide. Next, the cartridge 170 and distal end 155 of frame 150 of the stapler 100 are inserted into an entry port cut into the proximal lumen, or more typically inserted into the anus of the patient and positioned distal to the distal staple line in the lumen. The trocar shaft 180 of the stapler is extended through the lumen adjacent to the distal staple line. Then, the trocar shaft 180 is inserted into the anvil shaft 196. Next, the two sections of intestine are manipulated and stapled as previously described and sections of cut intestine containing staples along with any section of breakaway washer 200 are removed along with the stapler 100 from the intestine.

The tissue retention spring 10 of the present invention has numerous advantages. The spaces 28 between the coils 15 allow tissue and fluids to flow while the gap 210 is being shortened or closed. Closing a gap 210 in a circular stapler 100 typically results in the compression of the tissue and fluids within the gap 210. The presence of a conventional anvil bushing aggravates this problem since the anvil bushing occupies a volume which is unavailable for tissue or fluids to vent into. This venting feature of the spring 10 typically reduces the force required to close or shorten the gap 210 when compared with a stapler having a conventional anvil bushing. Another advantage of the spring 10 of the present invention is that the proximal end 20 may have a larger radius or diameter than the distal end 22. This allows the surgeon to more readily locate the coils 15 by palpation or otherwise and to further facilitate its use as a cutting guide. Yet another advantage of the spring 10 is that the coils 15 facilitate grasping and positive retention of the slippery interior mucosal layer of the intestine. Still another advantage of the tissue retention spring 10 is that the spring may have a longer length than a conventional anvil bushing since the spring 10 is compressible, thereby providing the surgeon with additional length in which to tie one or both ends of the intestine. The length of a conventional anvil bushing is inherently limited since an overly long conventional anvil bushing would adversely affect the minimum gap of the stapler when closed. As previously mentioned, an advantage of the tissue retention spring 10 of the present invention is that the spring 10 typically allows a stapler 100 to be closed with less force than when a conventional anvil bushing is used.

The tissue retention spring 10 may be manufactured using conventional manufacturing techniques including coil winding, die forming, casting and the like. The tissue retention spring 10 may be made from a material having an elongated cylindrical configuration such as a wire. The spring 10 of the present invention may be made from any medical grade material having sufficient mechanical and biocompatiblity properties effective to allow the tissue spring 10 to function. The materials include biocompatible materials such as polymer plastics, stainless steels, alloys, metals, plated carbon steel, plated metals, plated alloys and the like. It is particularly preferred to use a biocompatible material such as stainless steel.

The following example is illustrative of the principles and practice of the present invention although not limited thereto.

EXAMPLE

A mammal was prepared for surgery and anesthetized in accordance with conventional surgical procedures. A Veress needle was inserted into the abdominal cavity at the umbilicus. The abdomen was insufflated with $CO_2$. Insufflation was maintained during the procedure. A conventional 10/11 mm trocar was inserted at the umbilicus. A conventional 10 mm endoscope was inserted through a 10/11 mm trocar and connected to a light projector. A camera was mounted to the head of the endoscope. The camera allowed viewing (using a TV monitor) and recording (using a VCR) of the abdominal cavity and of all subsequent trocar insertions.

Secondary 5 mm or 10 mm conventional trocars were inserted as necessary in the caudal part of the abdomen to allow visualization and mobilization of the descending colon. The mesocolon was isolated and ligated or coagulated using conventional clips or electrocautery.

A stapled anastomosis was performed in the following manner: The bowel was transected with a conventional endoscopic linear cutter. The proximal staple line was trimmed to allow insertion of the anvil member 190. The anvil member 190 was detached from the stapler 100 and inserted through a trocar port. The anvil member 190 having tissue retaining spring 10 mounted was positioned in the proximal portion of bowel and secured with an ENDOLOOP ® suture. Excess tissue was trimmed, using the coils 15 of the tissue retention spring 10 as a cutting guide. The distal end of circular stapler 100 was inserted through the anus. The trocar shaft 180 was extended beside the distal staple line. The anvil shaft 196 was placed over the trocar shaft 180, aligned, snapped into place and tested for security. The gap 210 of stapler 100 was closed compressing spring 10, tightened to the appropriate staple height setting, and fired to perform the colonic anastomosis. The stapler 100 was removed from the colon. The resultant tissue donuts were examined for completeness. The colonic anastomosis was checked for patency and leakage.

It will be appreciate by those skilled in the art that the tissue retention spring can be used with conventional embodiments of circular staplers in addition to the circular stapler 100 disclosed herein. For example, while the circular stapler 100 utilizes an anvil member 190 having a shaft 196, other conventional staplers utilize an anvil member which does not have an anvil shaft. In those types of staplers, the trocar shaft mates directly with the anvil member. It is believed that the spring 10 of the present invention can be used with that type of stapler and would produce similar advantages.

Although this invention has been shown and described with respect to detailed embodiments thereof, it will be understood by those skilled in the art that various changes in form and detail thereof maybe made without departing from the spirit and scope of the claimed invention.

What is claimed is:

1. A method of using a circular stapler having an anvil, an anvil shaft, a staple cartridge and an actuating means to connect sections of intestine, comprising:
   positioning a tissue retention spring onto anvil shaft, wherein the spring comprises: a plurality of connected helical coils members defining a spring member, the coils separated by spaces, said spring member having a proximal end and a distal end and an axial length, said spring member having an axial passageway therethrough for mounting onto the anvil shaft;
   inserting the anvil and cartridge into adjacent sections of an intestine;
   tying at least one section of the intestine to the spring so that the intestine extends into at least one of the spaces between the coils of the spring; and, actuating the actuating means to staple the sections of the intestine together.

2. The method of claim 1 wherein the passage through the spring member comprises a cylindrical configuration.

3. The method of claim 1 wherein the diameter of the coils varies along the axial length of the spring.

4. The method of claim 1 wherein the diameter of the coils is constant along the axial length.

5. The method of claim 1 wherein the spaces between the coils are constant along the axial length.

6. The method of claim 1 wherein the spaces between the coils vary along the axial length.

7. A method of retaining tissue on a circular stapler having an anvil shaft, said method comprising:
   concentrically mounting a tissue retention spring on the anvil shaft, said tissue retention spring comprising a plurality of connected helical coils members defining a member, the coils separated by spaces, said member having a proximal end and a distal end and an axial length, said spring member having an axial passageway therethrough for mounting onto the anvil shaft;
   placing tissue about the spring; and,
   compressing the spring so that at least some of the tissue is engaged by the spring in the spaces between the coils.

8. The method of claim 7 further comprising the step of tying the tissue to the spring with at least one suture before compressing the spring.

9. The method of claim 7 wherein the passage through the spring member comprises a cylindrical configuration.

10. The method of claim 7 wherein the diameter of the coils varies along the axial length of the spring.

11. The method of claim 7 wherein the diameter of the coils is constant along the axial length.

12. The method of claim 7 wherein the spaces between the coils are constant along the axial length.

13. The method of claim 7 wherein the spaces between the coils vary along the axial length.

* * * * *